(12) United States Patent
Müller et al.

(10) Patent No.: US 7,510,685 B2
(45) Date of Patent: Mar. 31, 2009

(54) PARTICLE INJECTOR FOR A CELL SORTER

(75) Inventors: Torsten Müller, Berlin (DE); Stefan Hummel, Haseldorf (DE); Annette Pfennig, Berlin (DE)

(73) Assignee: Evotec Technologies GmbH (DE)

( * ) Notice: Subject to any disclaimer, the term of this patent is extended or adjusted under 35 U.S.C. 154(b) by 386 days.

(21) Appl. No.: 10/556,017

(22) PCT Filed: May 10, 2004

(86) PCT No.: PCT/EP2004/004984

§ 371 (c)(1),
(2), (4) Date: Jan. 23, 2006

(87) PCT Pub. No.: WO2004/099760

PCT Pub. Date: Nov. 18, 2004

(65) Prior Publication Data

US 2006/0115890 A1    Jun. 1, 2006

(30) Foreign Application Priority Data

May 9, 2003    (DE) ................ 103 20 870

(51) Int. Cl.
*B01L 3/00* (2006.01)
(52) U.S. Cl. ....................................... 422/99
(58) Field of Classification Search ............ 422/99
See application file for complete search history.

(56) References Cited

U.S. PATENT DOCUMENTS

| | | | |
|---|---|---|---|
| 4,954,715 A | 9/1990 | Zöld | |
| 5,138,181 A | 8/1992 | Lefevre et al. | |
| 5,351,118 A | 9/1994 | Spinell | |
| 5,489,506 A | 2/1996 | Crane | |
| 5,542,305 A | 8/1996 | Hollinger | |

(Continued)

FOREIGN PATENT DOCUMENTS

| | | |
|---|---|---|
| DE | 100 05 735 A1 | 8/2001 |
| WO | WO 02/11888 A2 | 2/2002 |
| WO | WO 02/065121 A1 | 8/2002 |
| WO | WO 02/081934 A2 | 10/2002 |
| WO | WO 03/078065 A1 | 9/2003 |

OTHER PUBLICATIONS

Müller, et al., "A 3-D microelectrode system for handling and caging single cells and particles", Biosensors & Bioelectronics 14 (1999), pp. 247-256.

*Primary Examiner*—Walter D Griffin
*Assistant Examiner*—Bobby Ramdhanie
(74) *Attorney, Agent, or Firm*—Caesar, Rivise, Bernstein, Cohen & Pokotilow, Ltd.

(57) ABSTRACT

The invention relates to a particle injector for introducing particles into a carrier flow of a microfluidic system, especially for injecting biological cells into the carrier flow of a cell sorter. The particle injector includes an inlet for receiving the carrier flow, an outlet for discharging the carrier flow including the introduced particles, a carrier flow channel which connects the inlet to the outlet, and an injection channel flowing into the carrier flow channel for introducing the particles into the carrier flow. The inventive particle injector is characterized in that the carrier flow channel has substantially no dead volume.

21 Claims, 12 Drawing Sheets

U.S. PATENT DOCUMENTS

Figure 1:
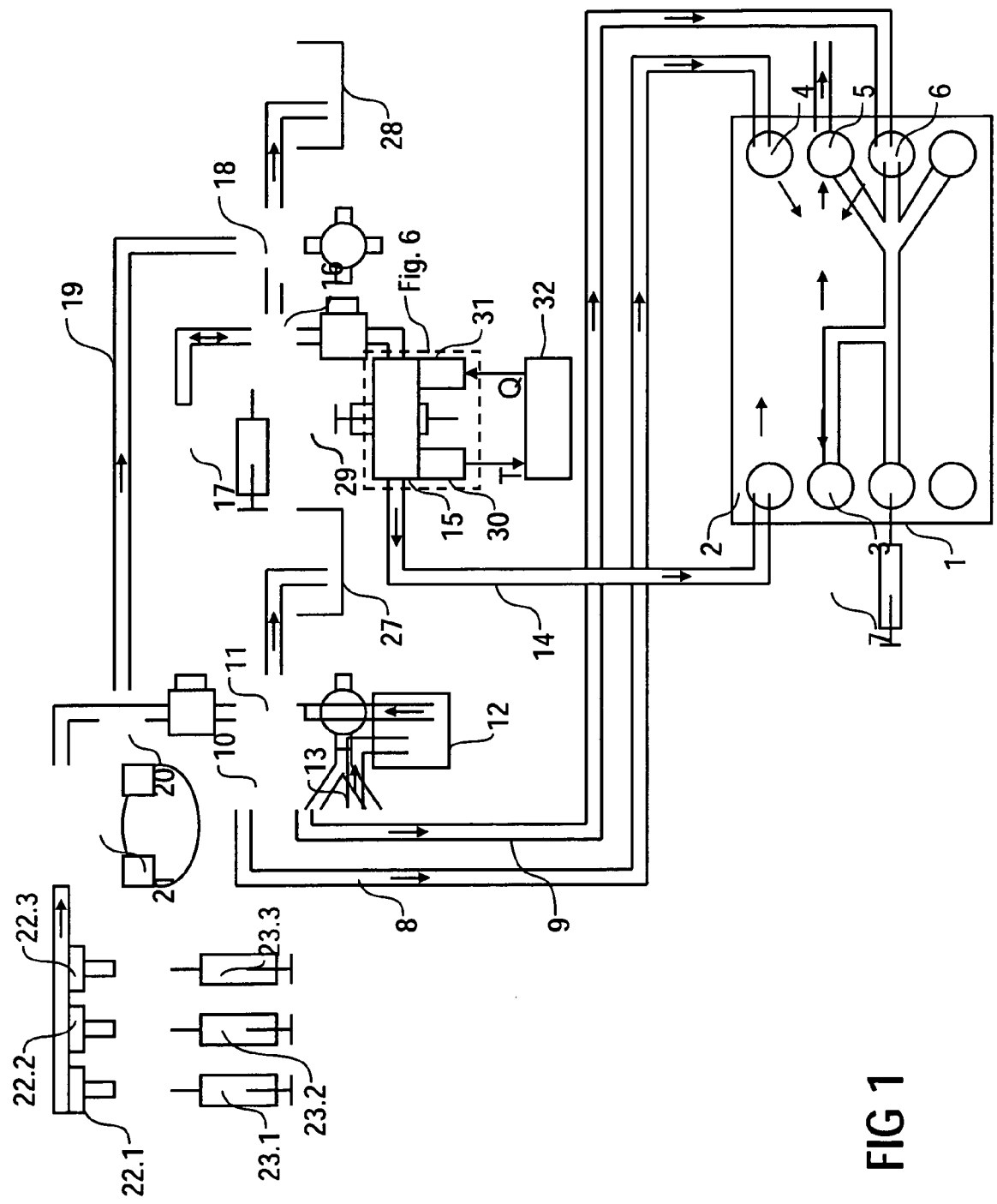

| | | |
|---|---|---|
| 5,672,481 A | 9/1997 | Minshall et al. |
| 5,714,059 A | 2/1998 | Seifert et al. |
| 6,270,641 B1 | 8/2001 | Griffiths et al. |
| 6,400,453 B1 | 6/2002 | Hansen |
| 2002/0036142 A1 | 3/2002 | Gascoyne et al. |
| 2003/0040105 A1 | 2/2003 | Sklar et al. |
| 2003/0108452 A1 | 6/2003 | Fuhr et al. |

PARTICLE INJECTOR FOR A CELL SORTER

BACKGROUND OF THE INVENTION

The invention relates to a particle injector for introducing particles into a carrier flow of a microfluidic system, in particular for injecting biological cells into the carrier flow of a cell sorter, according to the preamble of claim 1.

U.S. Pat. No. 5,489,506 discloses a cell sorter which enables biological cells to be separated dielectrophoretically in a carrier flow, whereby the dielectrophoretic effects used for separating are described for example in MÜLLER, T. et al. : "A 3-D microelectrode system for handling and caging single cells and particles", Biosensors & Bioelectronics 14 (1999) 247-256. The biological cells to be sorted are hereby injected by a particle injector into the carrier flow, whereby the carrier flow enters the particle injector via an inlet and later leaves it along with the injected biological cells via an outlet. The actual injecting of the biological cells to be sorted takes place through an injection needle, which is stuck through a septum in the particle injector and is guided coaxially into the carrier flow between the inlet and the outlet of the particle injector, so that the cells introduced via the injection needle are carried along by the carrier flow.

The disadvantage to this known particle injector is the loss of cells, arising from cell depositing in the particle injector. In the extreme case these cell deposits can result in clogging of the particle injector, impairing the feed of the carrier flow or to total obstruction. This has a particularly strong effect in fluidic systems with minimal feed rates of e.g. less than 200 μl/h.

The object of the invention therefore is to minimize the loss of cells through particle depositing in the above described known particle injector to prevent obstruction of the particle injector.

SUMMARY OF THE INVENTION

In particular a particle injector is to be provided, which selectively enables continuous or discontinuous injection of particles in a fluidic microchip ("Lab-on-Chip"), whereby the most uniform possible incessant (e.g. in the range of hours), loading of the system with particles is achieved. In addition, scattering of the particles is also ensured, thus counteracting interfering aggregate formation.

So as to prevent obstruction of the particle injector the carrier flow channel between the inlet of the particle injector and the outlet of the particle injector preferably has no dead volume, to avoid particles being stopped in the flow channel.

The carrier flow channel of the particle injector therefore preferably has a smooth inner contour without projections or depressions, which could hinder a laminar flow course. When considered as mathematically idealized the inner contour of the carrier flow channel therefore preferably has a constantly differentiable top surface.

The carrier flow channel in the particle injector between the inlet and the outlet preferably even has a constant cross-section of flow, since each change in cross-section in the carrier flow channel facilitates particles being stopped.

The cross-section of the carrier flow channel is preferably circular, however with the inventive particle injector the carrier flow channel can also be formed elliptical or angular.

In the preferred embodiment of the invention the injection channel for injecting the particles terminates obtusely and preferably right-angled in the carrier flow channel, so that the particle injector can also be described as a T injector. The advantage of such a geometric arrangement of the injection channel is that the carrier flow flowing in the carrier flow channel carries along the particles to be injected. The invention is however not limited with respect to the geometric arrangement of the injection channel to obtuse confluence of the injection channel in the carrier flow channel. It is also possible for example that the injection channel, as explained for the abovementioned U.S. Pat. No. 5,489,506, runs coaxially to the carrier flow channel so as to inject the particles coaxially into the carrier flow.

With the inventive particle injector the injection channel preferably serves not only for injecting the particles, but also for mechanical guiding of an injection needle, which can be stuck for example in through a septum and guided into the injection channel. The injection channel therefore preferably has an inner diameter, which is slightly greater than the outer diameter of the injection needle. With the injection channel of the particle injector the injection needle preferably forms a loose fit or transition fit to achieve good mechanical guiding of the injection needle.

Inserting the injection needle into the injection channel can be made easier in the inventive particle injector by a feeding-in aid, preferably comprising funnel-shaped cross-sectional widening of the injection channel. The feeding-in aid for the injection needle is preferably arranged in a separate component, attached detachably to the particle injector. By way of example this component serving as feeding-in aid can be screwed separately onto the particle injector or connected in some other way to the particle injector. By way of alternative however it is also possible that the feeding-in aid is arranged monobloc on the particle injector, so that a separate component as feeding-in aid can be dispensed with.

The abovementioned septum for sealing off the injection channel is preferably exchangeable and constructed multilayer. By way of example the septum can have a silicon core, coated on both sides with Teflon.

The fluidic contacting of the inventive particle injector occurs preferably by way of hoses, which are fastened on the inlet or respectively the outlet of the particle injector. With this fluidic contacting it is desirable that at the transition point between the hoses and the carrier flow channel as far as possible no cross-sectional leaks occur, so as to prevent depositing of particles there. To facilitate correct mounting of the hoses the inventive particle injector therefore preferably has at the inlet and/or the outlet a centering aid so that the hose is mounted as coaxially as possible to the carrier flow channel.

Such a centering aid can for example comprise a substantially hollow-cylindrical pick-up, which borders the carrier flow channel and is arranged coaxially to the carrier flow channel, whereby the inner diameter of the pick-up is greater by the wall thickness of the line to be connected than the inner diameter of the carrier flow channel. The line is therefore inserted into the hollow-cylindrical pick-up, which runs coaxially to the carrier flow channel and thereby ensures corresponding coaxial alignment to the line.

In a variant of the invention injecting the particles into the carrier flow channel takes place with respect to the gravity acting on the particle injector from top to bottom preferably vertically, whereby the injection channel is arranged on the top side of the particle injector. With such an arrangement of the injection channel above the carrier flow channel the effect of gravity favors introducing the particles into the carrier flow channel.

Here it is possible that the cross-section of the injection channel tapers conically down to the carrier flow channel, which also supports introducing an injection needle into the injection channel. In addition to this, the conical tapering of the injection channel also has a funneling function, as the particles converge in the lower region of the injection channel, so that no or only some particles remain caught in the injection channel, guaranteeing continuous particle feeding.

By way of example, the injection channel can taper to the carrier flow channel with a conic angle between 5° and 45°, whereby any intermediate values are possible.

In another variant of the invention the inlet of the carrier flow channel on the other hand is arranged on the underside of the particle injector, while the outlet of the carrier flow channel is located on the top side of the particle injector, so that the carrier flow is directed from the bottom to the top. The injection channel can hereby terminate to the side in the carrier flow channel, whereby the carrier flow channel preferably has a cross-section, which widens out from the inlet to the outlet. By way of example, the carrier flow channel can narrow conically to the inlet with a conic angle of between 5° and 45°, whereby any intermediate values are possible. Such narrowing of the cross-section of the carrier flow channel to the subjacent inlet is advantageous, since this counteracts any occluding of the carrier flow channel. In this way sedimentation effects in the carrier flow channel could lead to particle deposits in the lower region of the carrier flow channel. The narrowing of the cross-section in the lower region of the carrier flow channel however leads to a corresponding increase in the flow rate, thus extensively avoiding sedimentation deposits with the danger of occlusion.

Figure 12:
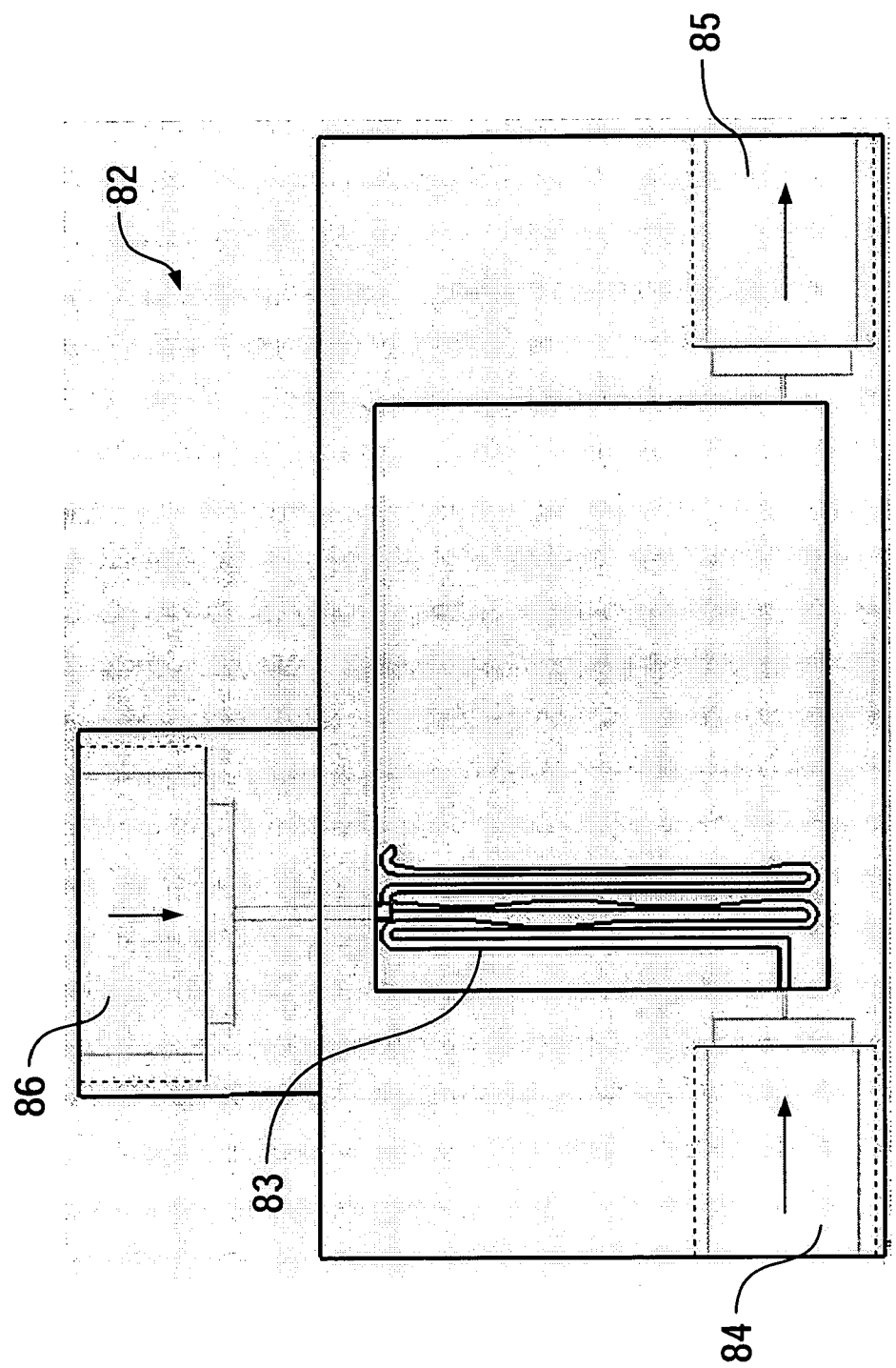
Figure 1:
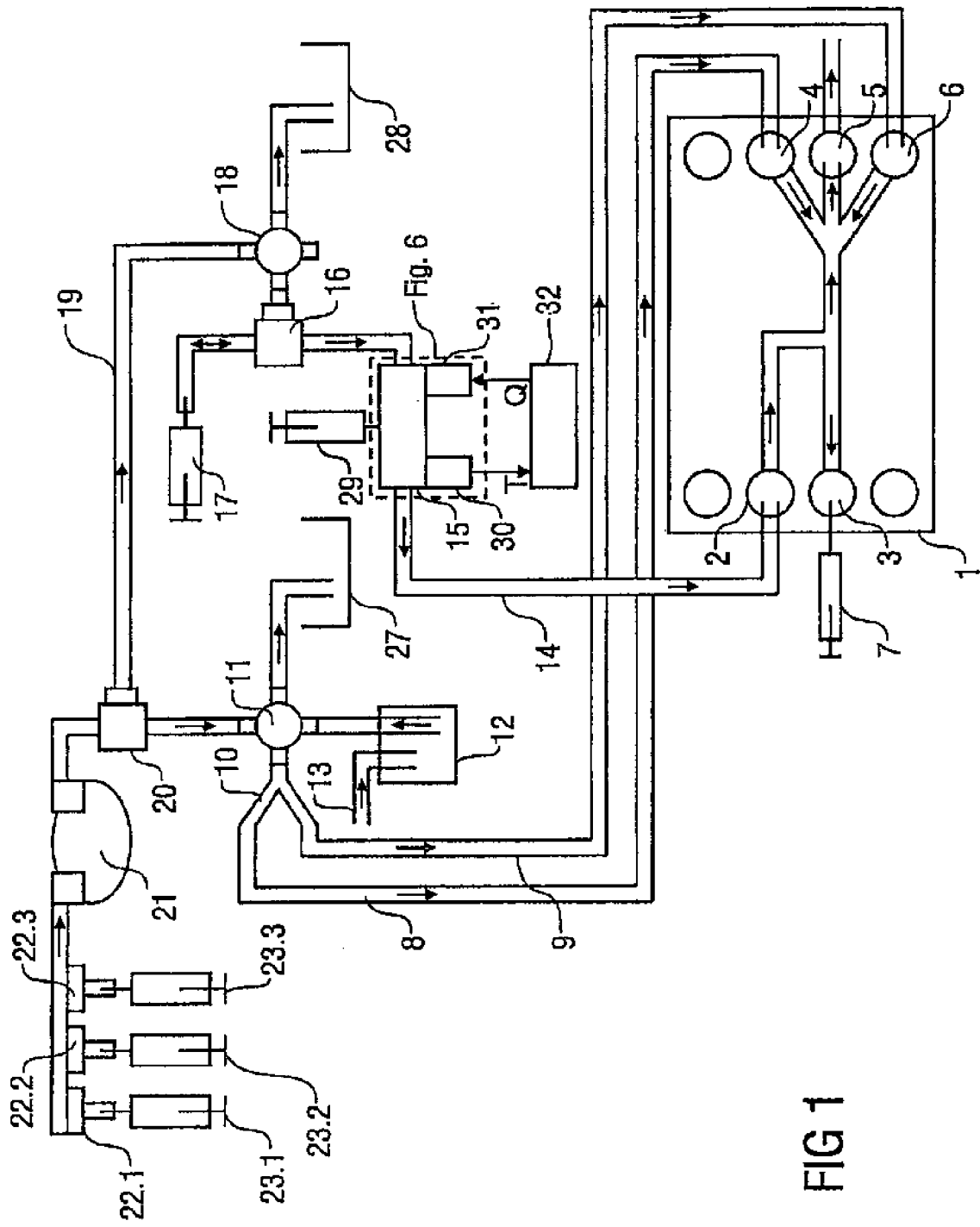
Figure 5:
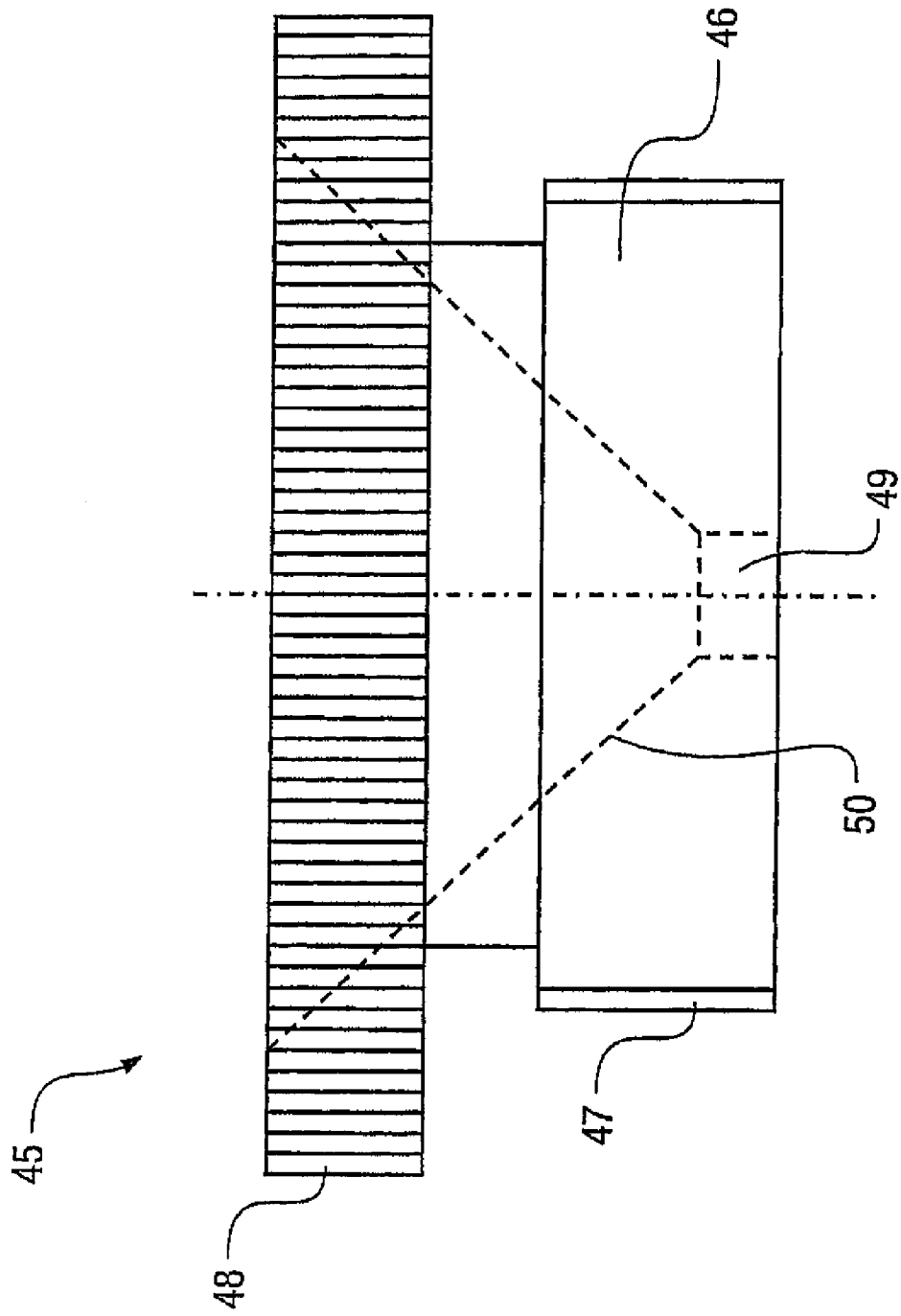
Figure 6:
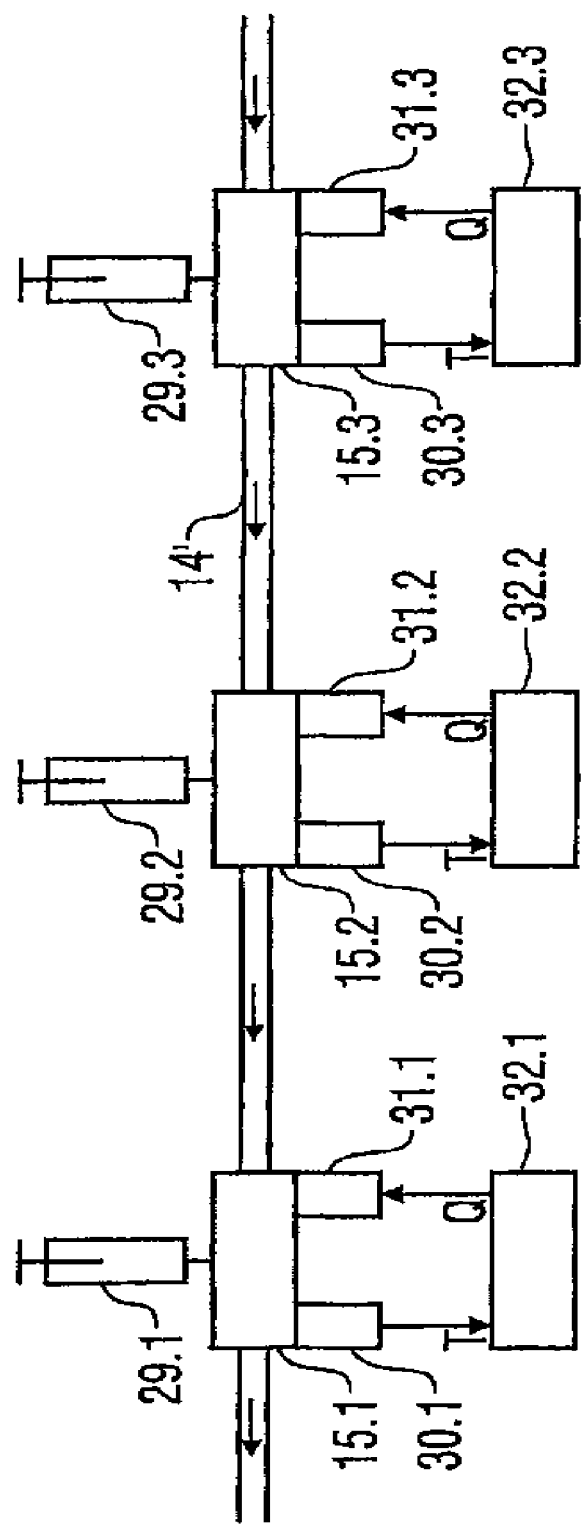

The carrier flow channel between the inlet and the outlet preferably has a volume of between 0.02 μl and 5 μl, where any intermediate values are possible. Though there is also the possibility that the volume of the carrier flow channel between the inlet and the outlet is between 20 μl and 50 μl, whereby likewise any intermediate values are possible. Furthermore, this volume can even be up to 1 ml or more, with volumes of between 0.02 μl and more than 1 ml possible.

There is also the possibility that the injection channel terminates obliquely upwards in the carrier flow channel, whereby the carrier flow channel preferably runs vertically. With the carrier flow channel flowing through from bottom to top the suspended particles are then carried along upwards and are flushed out of the particle injector. The angle between the injection channel and the carrier flow channel can hereby for example be between 10° and 80°, whereby any intermediate values are possible.

In addition to this, an agitation chamber, in which a magnetic stirring rod is located, can be arranged in the particle injector. This advantageously enables the carrier flow with the particles suspended therein in the agitation chamber to be intermixed with a conventional magnetic stirrer.

Several inlets and/or several outlets for the carrier flow can be arranged parallel to one another. In addition to this, there is also the possibility for several particle inlets to be provided.

The inventive particle injector can also have two carrier flow inlets, via which the two carrier flows are fed, whereby both carrier flow inlets preferably terminate in a single carrier flow outlet. Both the carrier flow inlets can hereby be arranged laterally and opposite one another.

It is a further advantage if the carrier flow channel in the particle injector is guided meandering between the inlet and the outlet. Due to the narrowing and widening in the carrier flow channel the sedimentizing of the particles in the carrier flow channel is countered, so that the suspended particles move uniformly and continuously.

It should also be mentioned that the inventive particle injector can preferably be autoclaved so as to enable sterilization of the particle injector. A suitable material for the particle injector therefore is preferably PEEK, however the inventive particle injector can also comprise other materials.

It is also advantageous if the particle injector comprises a heat-conductive material, so as to measure or influence the temperature of the particle injector. The particle injector is preferably therefore connected to a temperature sensor and/or a tempering element, whereby the tempering element preferably enables both heating and also cooling of the particle injector and for example may comprise a Peltier element.

The inventive particle injector can be made for example by machining methods or an injection molding process, however the invention is not limited to these particular manufacturing methods.

In addition to this, the invention also comprises a microfluidic system with the inventive particle injector, whereby the particle injector is preferably arranged in a carrier flow line, terminating in a cell sorter.

In an embodiment of such a microfluidic system several inventive particle injectors can be arranged in the carrier flow line behind one another, so that different particles can be injected successively. Instead of particles specific reagents or reaction solutions can also be added via the individual particle injectors in each case.

It should also be mentioned that the term particle used within the scope of the invention is to be understood generally, and is not limited to individual biological cells. Rather, the inventive particle injector can operate with various types of particles, in particular synthetic or biological particles. Specific advantages will emerge if the particles include biological materials, therefore for example biological cells, cell groups, cell constituents or biologically relevant macromolecules, in each case if required in combination with other biological particles or synthetic carrier particles.

Synthetic particles can include solid particles, liquid particles separated out from the suspension medium, or multiphase particles, which form a separate phase relative to the suspension medium in the carrier flow channel.

BRIEF DESCRIPTION OF SEVERAL VIEWS OF THE DRAWINGS

Other advantageous further developments of the invention are characterized in the independent claims or are explained in greater detail hereinbelow along with the description of the preferred embodiments of the invention by way of the figures, in which:

FIG. 1 illustrates a cell sorter with an inventive particle injector,

FIGS. 2 to 4 illustrate cross-sectional views of various alternative embodiments of the particle injector, FIG. 5 illustrates a side elevation of a feeding-in aid for easing insertion of an injection needle into the inventive particle injectors, FIG. 6 illustrates a variant of a microfluidic system with an inventive particle injector, FIG. 7 illustrates a further embodiment of an inventive particle injector with integrated magnetic stirring rods, FIG. 8 illustrates a further embodiment of an inventive particle injector with angled guiding of the carrier flow, FIG. 9 illustrates an embodiment of an inventive particle injector, in which the particles are injected obliquely into the carrier flow, FIG. 10 illustrates another embodiment of an inventive particle injector with two opposing carrier flow feeds, FIG. 11 illustrates a perspective illustration of an inventive particle injector, and FIG. 12 illustrates a further embodiment of an inventive particle injector with meandering guiding of the carrier flow channel.

DETAILED DESCRIPTION OF PREFERRED EMBODIMENTS

The schematic illustration in FIG. 1 shows an inventive cell sorter, which sorts biological cells dielectrophoretically by means of a microfluidic sorter chip 1.

The techniques of the dielectrophoretic influence of biological cells are described for example in MÜLLER T. et al. : "A 3-D microelectrode system for handling and caging single cells and particles", Biosensors & Bioelectronics 14 (1999) 247-256, so that a detailed description of the dielectrophoretic processes in the sorter chip 1 are dispensed with hereinbelow, and this is pointed out with respect to the above publication.

The sorter chip 1 has several terminals 2-6 for fluidic contacting whereby fluidic contacting of the terminals 2-6 is described in DE 102 13 272, the content of which is incorporated herein by reference.

The terminal 2 of the sorter chip 1 serves to receive a carrier flow with the biological cells to be sorted, while the terminal 3 of the sorter chip 1 serves to discard the selected biological cells, which are no longer being inspected on the sorter chip 1. The selected biological cells can be intercepted by an injection 7, which can be connected to the terminal 3 of the sorter chip 1. The output 5 of the sorter chip 1 on the other hand serves to reject the interesting biological cells, which are then further processed or inspected.

The purpose of the terminals 4 and 6 of the sorter chip 1 is to feed a so-called shell flow, whereof the task is to guide the selected biological cells to the terminal 5 of the sorter chip 1. With respect to the functioning of the shell flow reference is made to the German patent application DE 100 05 735, so that a detailed description of the functioning of the shell flow can be omitted.

The terminals 4 and 6 of the sorter chip are connected via two shell flow lines 8, 9, a Y piece 10 and a four-way valve 11 with a pressurized container 12, in which there is a cultivation medium for the shell flow. Instead of the cultivation medium, however, in the pressurized container 12 there can also be a so-called manipulation buffer.

The pressurized container 12 is set on a compressed air line 13 at superpressure, so that with corresponding adjustment of the four-way valve 11 the cultivation medium in the pressurized container 12 flows via the Y piece 10 and the shell flow lines 8, 9 to the terminals 4, 6 of the sorter chip 1.

Figure 2:
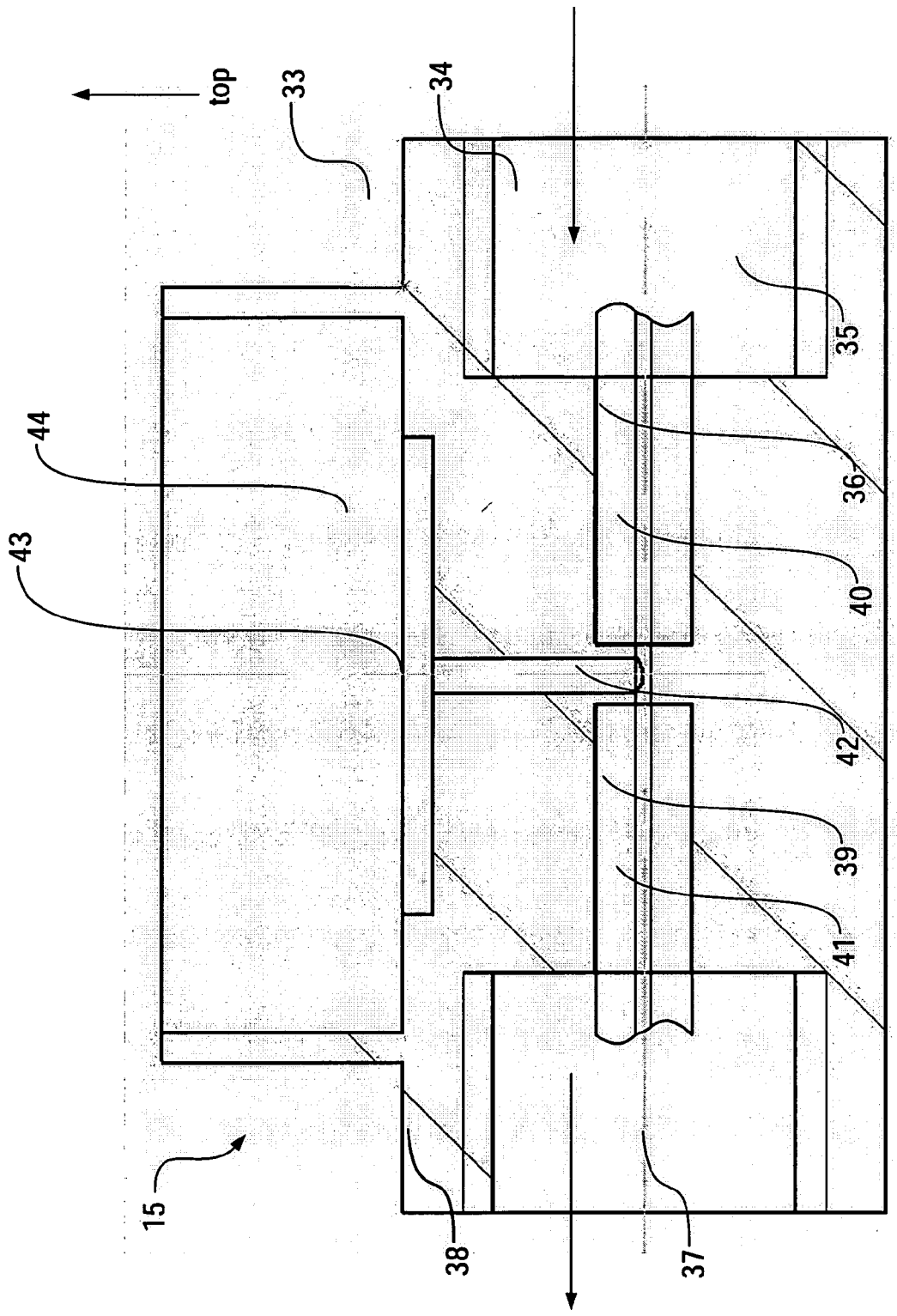
Figure 3:
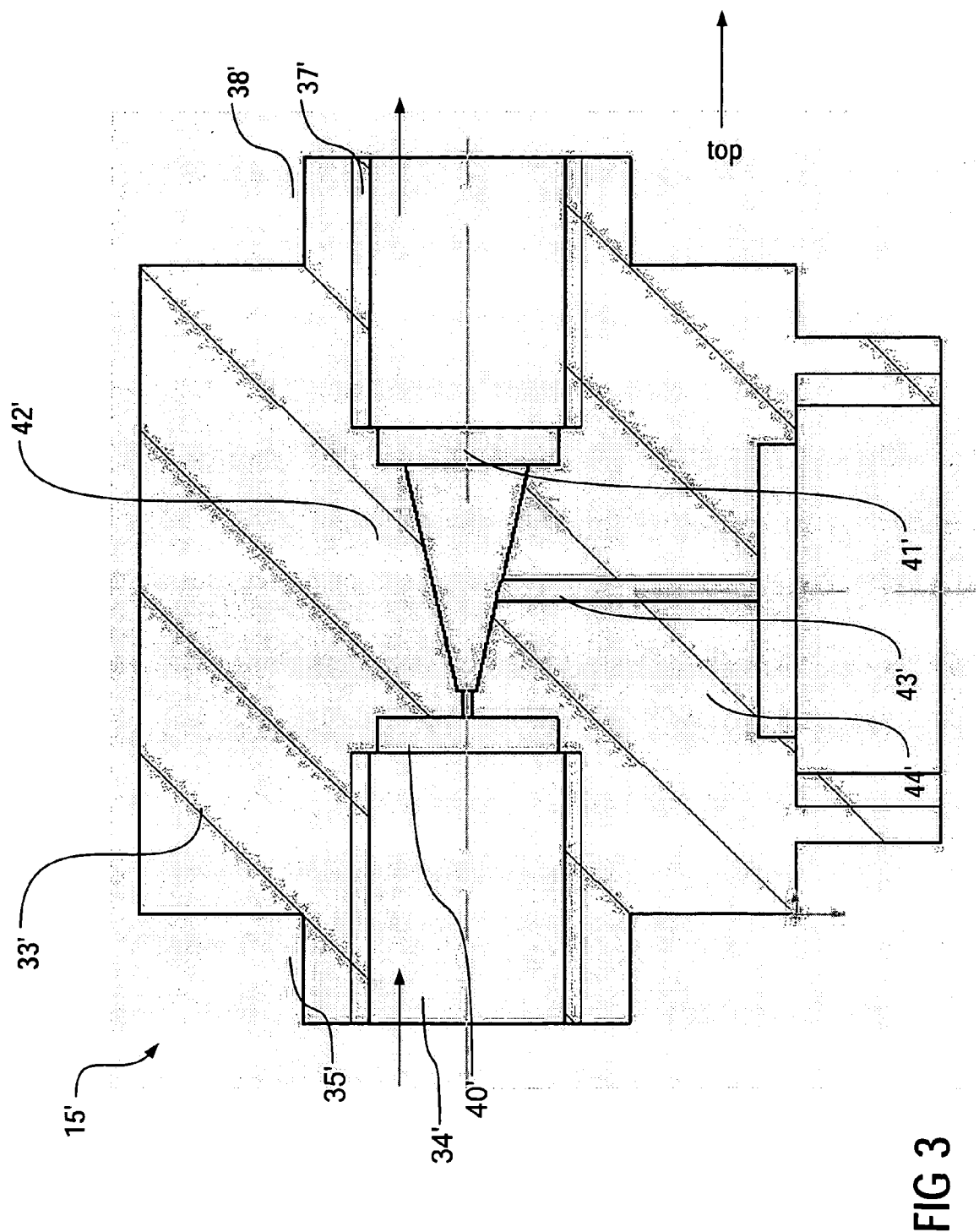
Figure 4:
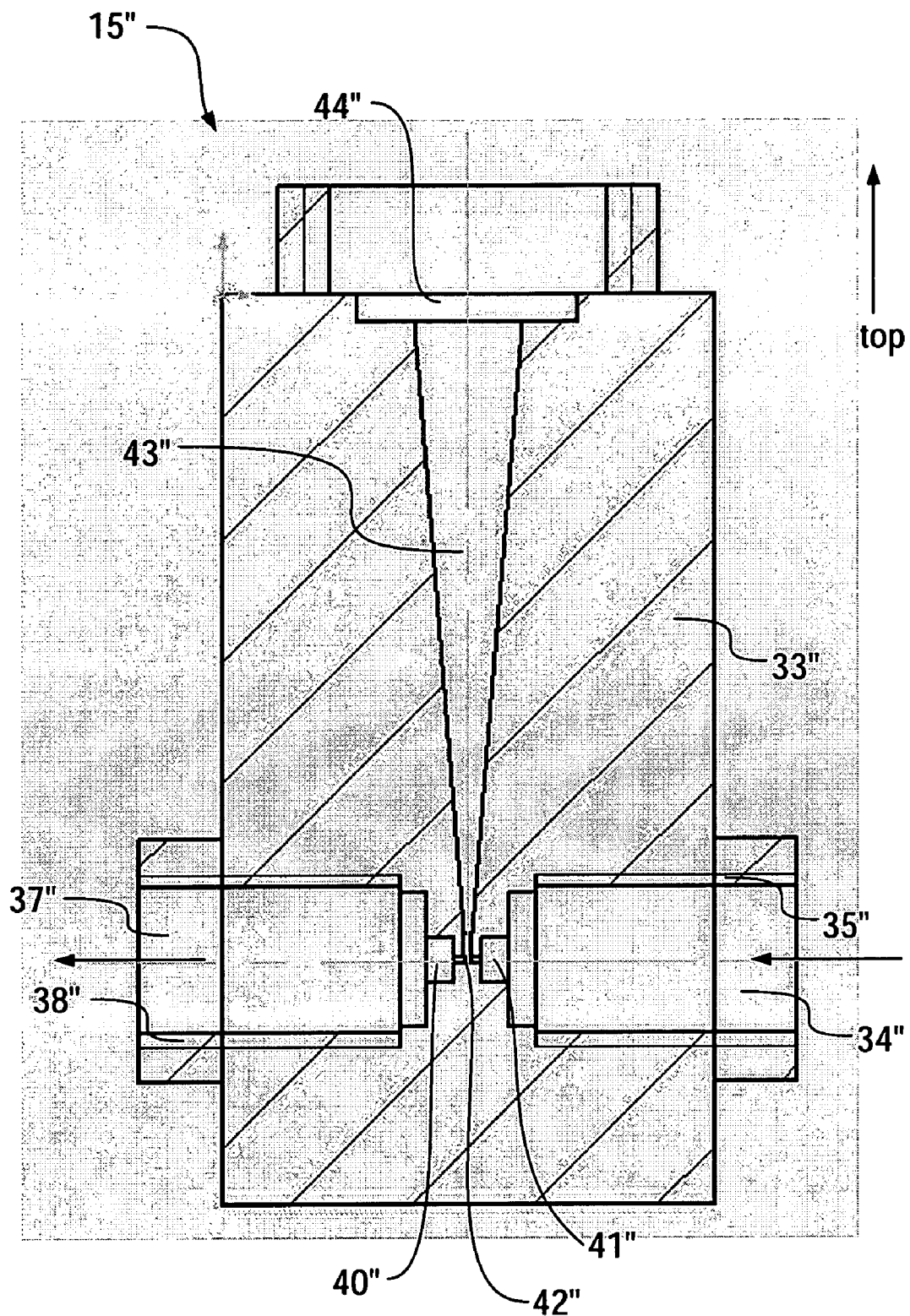
Figure 5:
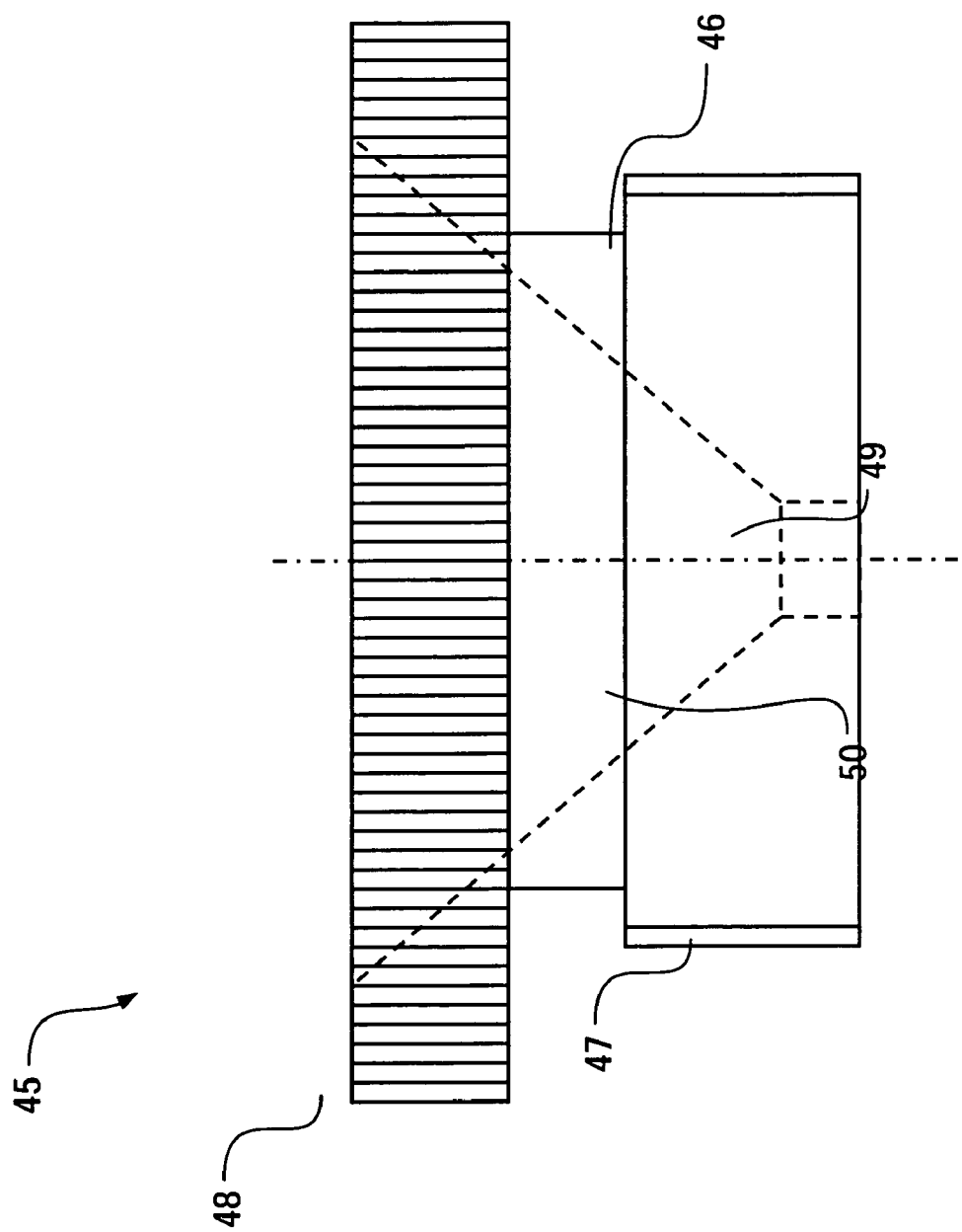
Figure 6:
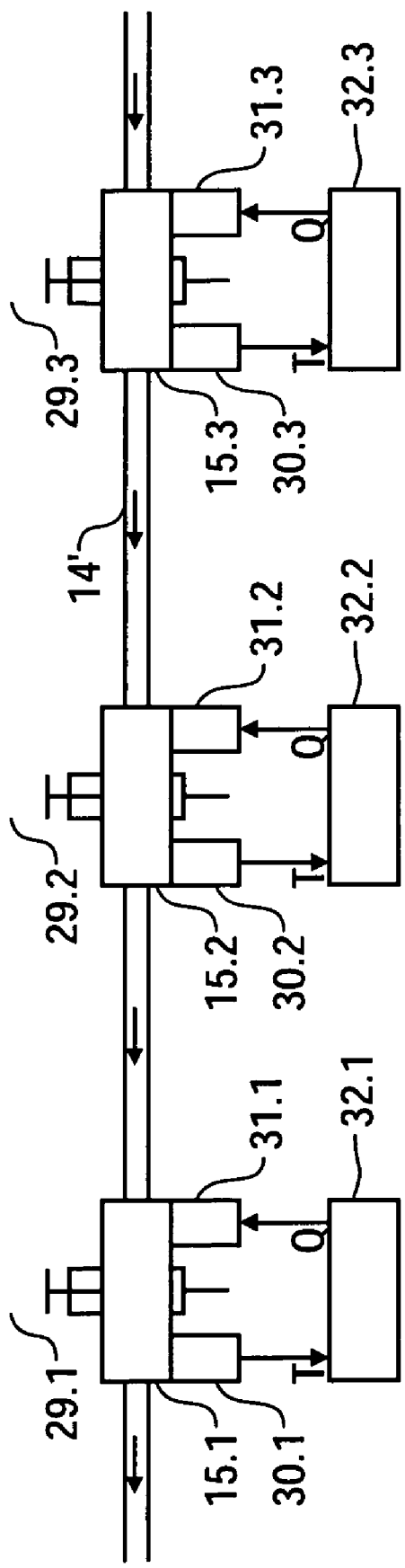
Figure 7:
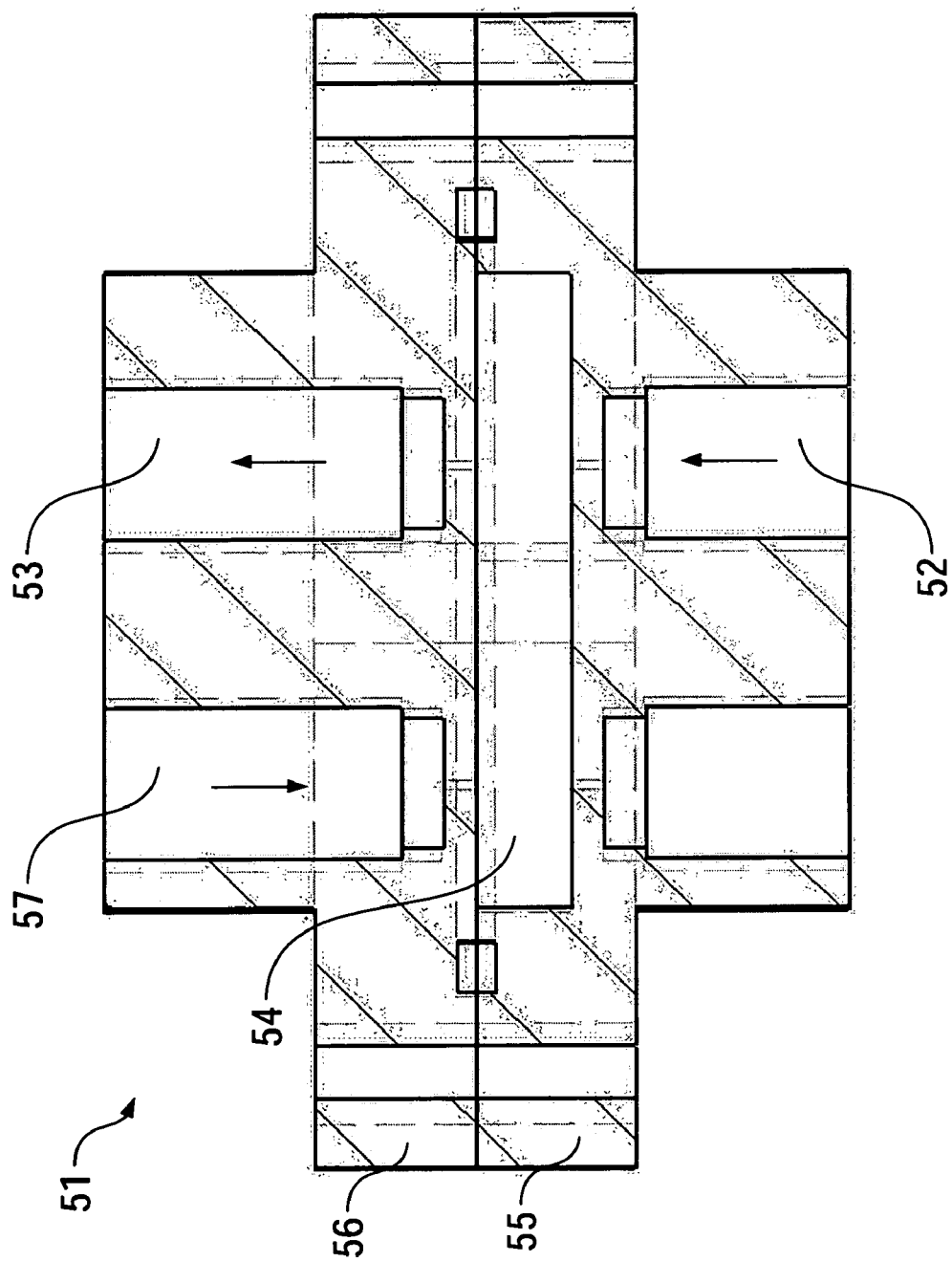

The terminal 2 of the sorter chip 1 by way of comparison is connected via a carrier flow line 14 to a particle injector 15, whereof various alternative embodiments are illustrated in FIGS. 2 to 4 and are described hereinbelow in greater detail.

Upstream the particle injector 15 is connected via a T piece 16 to a carrier flow injection 17, driven by machine and injecting a preset liquid flow of a carrier flow.

In addition to this, the T piece 16 upstream is connected via a further four-way valve 18 and a shell flow line 19 to a three-way valve 20. The three-way valve 20 enables flushing of the shell flow lines 8, 9 as well as the carrier flow line 14 prior to actual running.

For this purpose the three-way valve 20 upstream is connected via a peristaltic pump 21 to three three-way valves 22.1-22.3, to which in each case an injection reservoir 23.1-23.3 is attached. The injection reservoirs 23.1-23.3 hereby serve to feed a filling flow for flushing the entire fluidics system prior to actual operation, whereby the injection reservoir 23.1 contains 70% ethanol, whereas the injection reservoir 23.2 contains Aqua destillata as filling flow substance. The injection reservoir 23.3 finally contains a buffer solution as filling flow substance, whereby alternatively another manipulation solution can also be used as filling flow substance, such as for example a physiological saline solution.

Also, the cell sorter has a collection container 27 for excess shell flow as well as a collection container 28 for excess filling flow.

Hereinafter the flushing procedure is first described, which is carried out prior to actual operation of the cell sorter so as to free the shell flow line 8, 9, the carrier flow line 14 and the remaining fluidics system of the cell sorter of air bubbles and contaminants.

For this purpose first the three-way valve 22.1 is opened and ethanol is injected from the injection reservoir 23.1 as a filling flow, whereby the ethanol is conveyed by the peristaltic pump 21 first to the three-way valve 20. During the flushing procedure the three-way valve 20 is adjusted such that part of the filling flow forwarded by the peristaltic pump 21 is conveyed via the filling flow line 19, while the remaining portion of the filling flow conveyed by the peristaltic pump 21 reaches the four-way valve 11. Both four-way valves 11, 18 are again adjusted such that the filling flow is lead through the shell flow lines 8, 9 and the carrier flow line 14. Cultivation medium flows from the pressurized container 12 into the collection container 27 to briefly inundate the lines.

After the above described flushing of the cell sorter with ethanol flushing with Aqua destillata or respectively buffer solution takes place in the same way, whereby in each case the three-way valves or respectively 22.2 or respectively 22.3 are opened.

With the above described flushing procedure excess filling flow can be diverted by the four-way valve 18 to the collection container 28.

Following the flushing procedure the three-way valves 22.1-22.3 are closed and the peristaltic pump 21 is switched off.

To introduce the sorting operation the four-way valve 11 is adjusted such that the pressurized container 12 is connected to the Y piece 10, such that the cultivation medium in the pressurized container 12 is pressed into the shell flow lines 8, 9 on account of the excess pressure prevailing in the pressurized container 12.

Further to this, during the sorting operation the four-way valve 18 is adjusted such that there is no flow connection between the T piece 16 and the four-way valve 18.

The carrier flow injected by the carrier flow injection 17 then flows via the T piece 16 into the particle injector 15, whereby biological cells are injected into the carrier flow by a further injection 29. Next the carrier flow flows with the injected biological cells from the particle injector 15 via the carrier flow line 14 to the terminal 2 of the sorter chip.

It should also be mentioned that attached to the particle injector 15 is a temperature sensor 30 for measuring the temperature T of the particle injector 15.

In addition to this, a tempering element 31 in the form of a Peltier element, for heating or cooling the particle injector 15, is located on the particle injector 15.

The heating or respectively cooling energy Q is hereby preset by a temperature controller 32, which is connected at the inlet side to the temperature sensor 30 and resets the temperature T of the particle injector 15 to a preset nominal value.

The embodiment of the particle injector 15 illustrated in FIG. 2 will now be described hereinbelow.

The particle injector 15 has a basic body 33 made of PEEK, which can be autoclaved and thus enables easy and/or multiple sterilization.

For taking up the carrier flow the particle injector 15 has an inlet 34 with an inner thread 35, into which a screw flange of a terminal hose 36 can be screwed, with the screw flange not being illustrated here for the sake of clarity.

For discharging the carrier flow with the injected biological cells the particle injector 15 has an outlet 37 with an inner thread 38, in which likewise a screw flange of a terminal hose 39 can be screwed, with the screw flange of the terminal hose 39 likewise not being illustrated here for the sake of clarity.

To make mounting of both hoses 36, 39 easier the particle injector 15 in each case has a centering aid 40, 41, comprising a cylindrical pick-up and bordering the inlet 34 or respectively 37. Running between both centering aids 40, 41 is a carrier flow channel 42 coaxially to both centering aids 40, 41, whereby the inner diameter of both centering aids 40, 41 is larger by the wall thickness of both connecting hoses 36, 39 than the inner diameter of the carrier flow channel 42. With mounting the connecting hoses 36, 39 the former are therefore placed in the centering aids 40, 41 such that at the point of impact between the hoses 36, 39 and the carrier flow channel 42 no leaks occur, which extensively prevents occlusion of the carrier flow channel 42.

In the carrier flow channel 42 an injection channel 43, into which an injection needle of the injection 29 can be introduced for injecting biological cells, terminates at a right angle to the carrier flow channel 42, whereby the injection needle of the injection 29 punctures a septum 44.

FIG. 3 shows an alternative embodiment of an injector 15', which substantially matches with the above described embodiment illustrated in FIG. 2. In the interests of avoiding repetition reference is therefore made hereinbelow to the above described description to FIG. 2, whereby the same reference numerals are used as in FIG. 2 for corresponding parts, which are distinguished for differentiating only by an apostrophe.

A particularity of the particle injector 15' comprises the inlet 34' for the carrier flow being arranged on the underside of the particle injector 15', while the outlet 37' for the carrier flow with the injected biological cells being located on the top side of the particle injector 15'. The carrier flow therefore runs in the particle injector 15' vertically from bottom to top, whereby the injection channel 43' terminates to the side in the carrier flow channel 42'.

A further particularity of the particle injector 15' is that the cross-section of the carrier flow channel 42' tapers from top to bottom, so that the flow rate of the carrier flow in the carrier flow channel 42' accordingly increases from top to bottom. Sedimentation deposits on the underside of the carrier flow channel 42' are counteracted by this increase in the flow rate in the carrier flow channel 42'.

There is also the possibility that at the lower end of the funnel-shaped narrowing of the injection channel 43' just above the carrier flow channel 42' there is a valve arranged, enabling discontinuous particle feeding.

FIG. 4 shows another alternative embodiment of a particle injector 15", which likewise substantially matches the above described particle injector 15 shown in FIG. 2. To avoid repetition therefore hereinbelow reference is also made to the above description to FIG. 2, whereby the same reference numerals are used for corresponding parts, which are distinguished for differentiating only by two apostrophes.

A particularity of the particle injector 15" comprises the cross-section of the injection channel 43" widening upwards to its terminal opening, so that the injection needle of the injection 29 can be introduced more easily.

In addition to this, the conical narrowing of the injection channel 43" also has a funnel function, since the particles converge in the lower region of the injection channel 43", so that no or only some particles remain in the injection channel 43", ensuring continuous particle feeding.

The cross-sectional widening of the injection channel 43" further offers the advantage that the injection channel 43" has an additional injection volume in the range of 5-100 μl.

Finally, FIG. 5 shows an exemplary feeding-in aid 45 for the injection needle of the injection 29, whereby the feeding-in aid 45 is designed as a separate component. The feeding-in aid 45 has on its underside a cylindrical section 46 with an external thread 47, which can be screwed into a corresponding inner thread of the particle injector 15' or respectively 15", in order to attach the feeding-in aid 45 on the particle injector 15' or respectively 15".

The feeding-in aid 45 is screwed in manually via knurling 48, arranged on an upper section of the feeding-in aid 45.

In the feeding-in aid is a projection 49 of the injection channel 43 or respectively 43', which transitions at its top side into a funnel-shaped widening 50, to facilitate introducing the injection needle of the injection 29.

FIG. 6 finally shows a modification of the region outlined in dashed lines in FIG. 1, so that hereinbelow reference is made to the description to FIG. 1 to avoid repetition. In addition to this, the same reference numerals, which are distinguished to avoid repetition only by additional indices, are used for corresponding components.

A particularity of this modification comprises three particle injectors 15.1-15.3 being arranged successively in the carrier flow line 14', so that three different particles can be injected into the carrier flow.

FIG. 7 shows a further embodiment of an inventive particle injector 51 with an inlet 52 for receiving a carrier flow and an outlet 53 for discharging the carrier flow with particles suspended therein.

The inlet 52 terminates in the particle injector 51 in an agitation chamber 54, in which a magnetic stirring rod is located, not illustrated here for the sake of clarity. The carrier fluid in the agitation chamber 54 can therefore be agitated by a conventional magnetic stirrer, resulting in thorough intermingling of the carrier fluid with the particles suspended therein. The agitation rate is hereby selected such that the particles suspended in the carrier fluid are not damaged by the stirring procedure.

The particle injector 51 comprises a lower part 55 and an upper part 56, whereby the agitation chamber 54 is arranged in the lower part 55. In the mounted state the lower part 55 is connected firmly to the upper part 56 and sealed by an O ring located in between.

The particles are injected into the carrier flow via an injection channel 57, which terminates in the agitation chamber 54 to the side near the outlet 53'. The injection channel 57 can hereby be closed by a septum, as already described hereinabove.

In this embodiment the inlet 52 for the carrier flow is on the underside of the particle injector 51, whereas the outlet 53 is arranged on the top side, so that the carrier flow flows through the particle injector 51 from bottom to top.

Alternatively, however, it is also possible that the inlet 52 is arranged on the top side of the particle injector 51, while the outlet 53 is located on the underside of the particle injector 51, such that the carrier flow slows through the particle injector 51 from top to bottom.

Hereby, parallelizing is also possible and between the agitation chamber 54 and the outlet 53 a valve can be arranged to enable discontinuous discharge.

Figure 8:
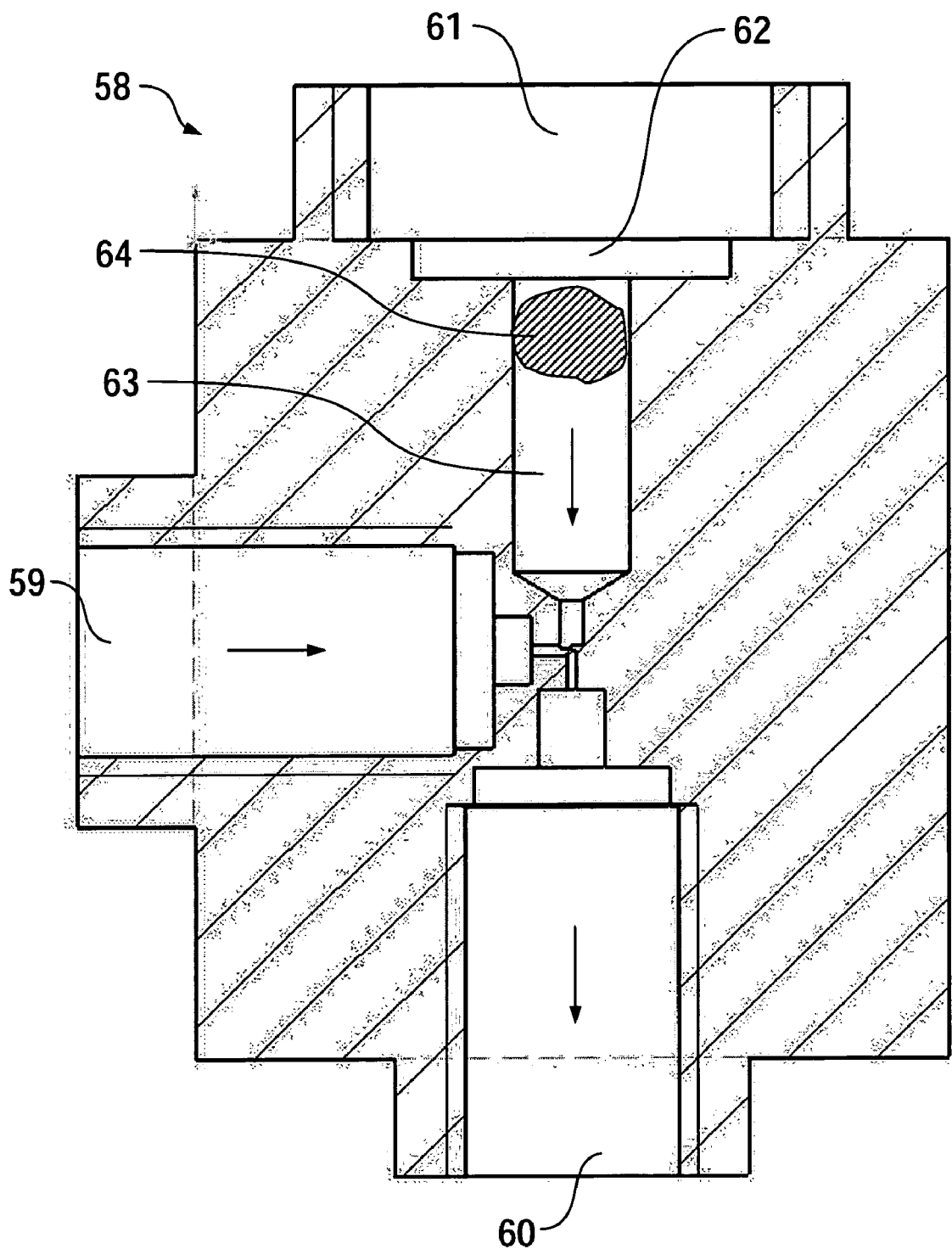

FIG. 8 shows a further embodiment of an inventive particle injector 58 with an inlet 59 for receiving a carrier flow and an outlet 60 for discharging the carrier flow with particles suspended therein.

The inlet 59 is hereby arranged on the left side of the particle injector 58, while the outlet 60 is located on the underside of the particle injector 58. The carrier flow is therefore deflected down into the particle injector 58 by 90°.

For particle injection the particle injector 58 has an injection terminal 61, arranged on the top side of the particle injector 58 and closed by a septum 62. The septum 62 is penetrated by an injection needle for injecting particles into the carrier flow.

Located under the septum 62 in the particle injector 58 are a cylindrical sedimentation space 63, in which the suspended particles illustrated by hatching 64 sedimentize downwards due to gravity, and enter the carrier flow depending on the sedimentation rate. The sedimentation space 63 can however alternatively be designed conically.

Figure 9:
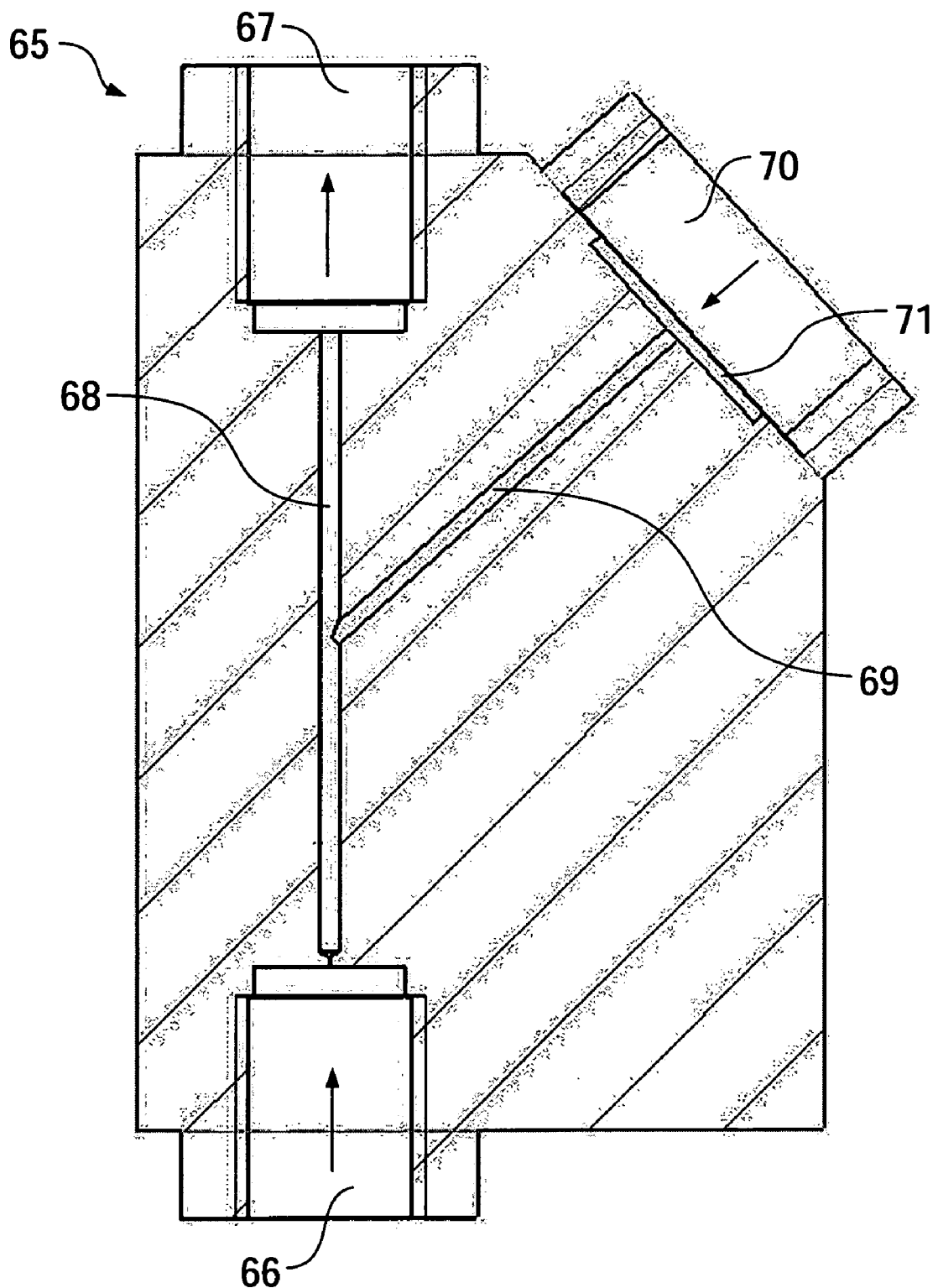

FIG. 9 shows a further embodiment of an inventive particle injector 65 with an inlet 66 for the carrier flow and an outlet 67 for discharging the carrier flow with the particles suspended therein.

The inlet 66 for the carrier flow is located on the underside of the particle injector 65, while the outlet 67 is arranged on the top side, so that the carrier flow flows through the particle injector 65 from bottom to top.

The inlet 66 is connected via a carrier flow channel 68 to the outlet 67, whereby an injection channel 69, which goes out from an injection terminal 70, terminates in the carrier flow channel 68 obliquely from above, whereby the injection terminal 70 is closed by a septum 71 in the above described manner.

A particle suspension, which is distributed in the long-stretched-out injection channel 69, is injected through the injection terminal 70. Due to gravity the particles begin to sink. A jet, which already receives sunken and other still sinking particles and flows upwards out of the particle injector 65, is formed by the carrier flow, which enters the particle injector 65 from below and via the narrowing of the carrier flow channel 68, as shown. In the long-stretched-out carrier flow channel 68 the resulting carrier flow rates and injected volumes can vary, depending on length and diameter.

Figure 10:
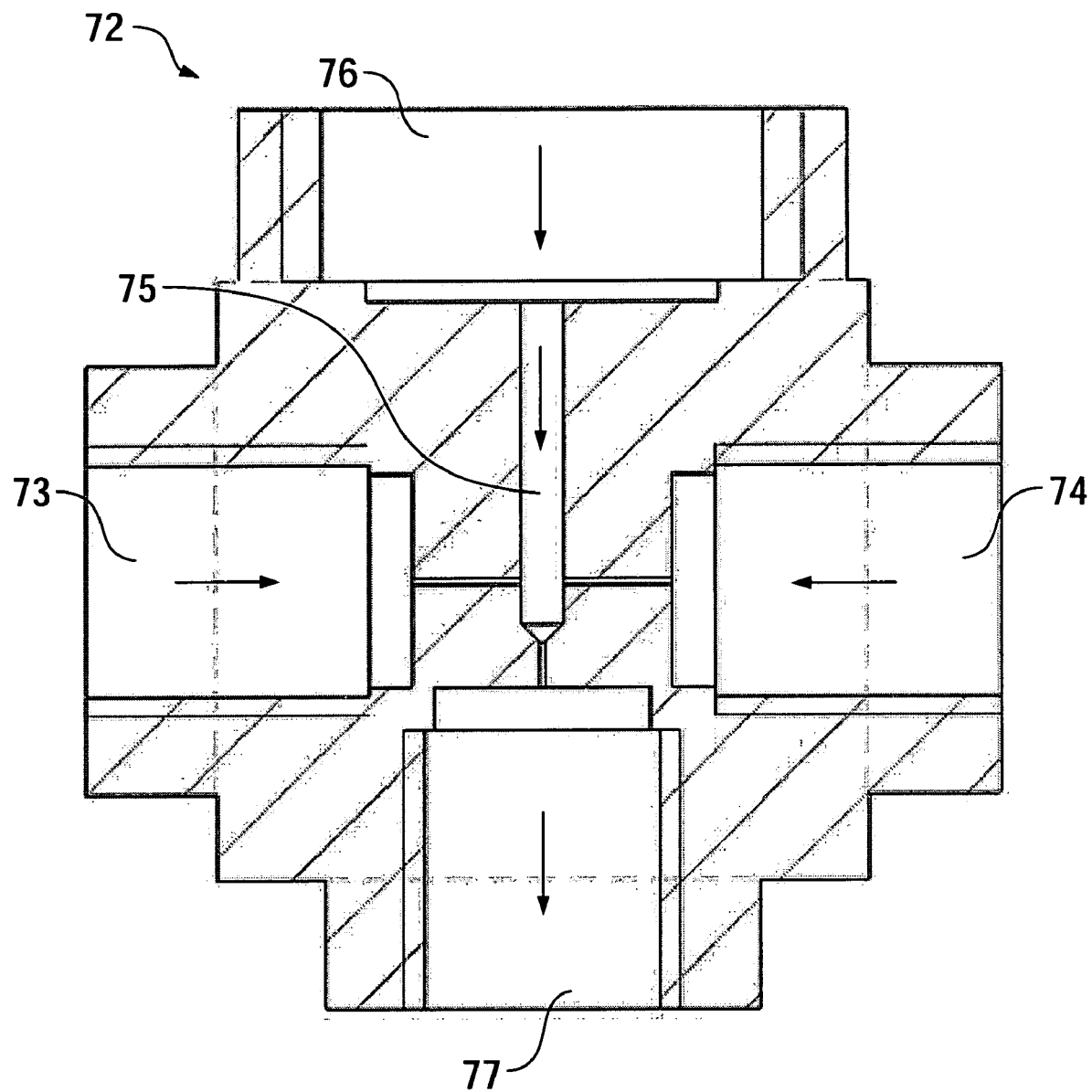

FIG. 10 shows a further embodiment of an inventive particle injector 72 with two laterally arranged, opposing inlets 73, 74 for receiving two carrier flows, whereby both inlets 73, 74 terminate in the middle of the particle injector 72 into a perpendicular cylindrical injection channel 75.

The injection channel 75 goes from an injection terminal arranged on the top side of the particle injector 72 76 and terminates on the underside of the particle injector 72 in an outlet 77 for discharging the carrier flow with the particles suspended therein.

Figure 11:
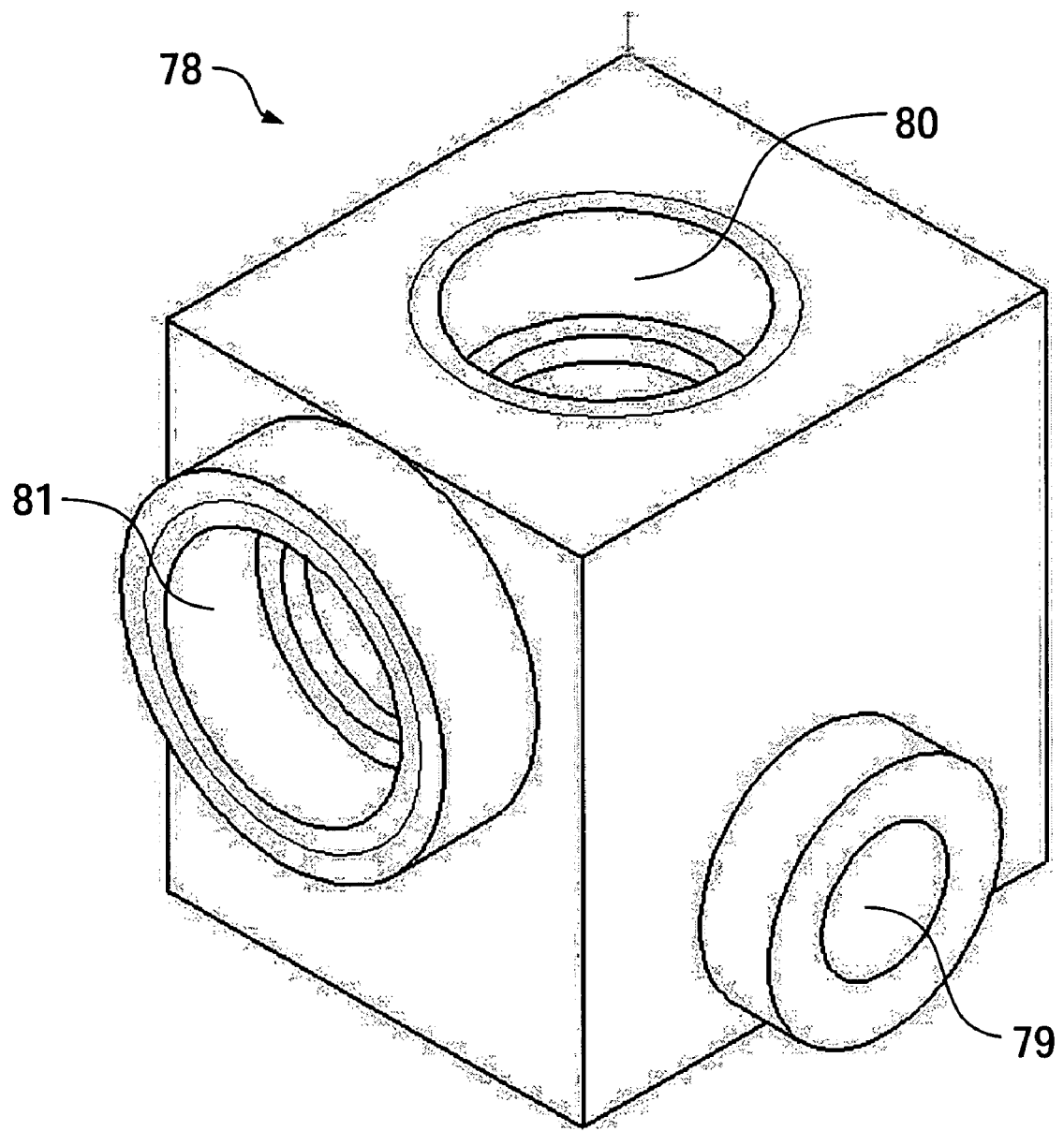

FIG. 11 shows a perspective illustration of a further embodiment of an inventive cuboid particle injector 78 with an inlet 79 for receiving a carrier flow and an outlet 80 for discharging the carrier flow with particles suspended therein, whereby the inlet 79 inside the particle injector 78 is connected to the outlet 80 by a carrier flow channel.

The inlet 79 is hereby located on the side of the particle injector 78 in the lower third, whereas the outlet 80 is arranged centrally on the top side of the particle injector 78.

Situated on the front side of the particle injector 78 is an injection terminal 81, by means of which particles can be injected into the carrier flow.

FIG. 12 finally shows an embodiment of an inventive particle injector 82 with a meandering guide for a carrier flow channel 83 between an inlet 84 and an outlet 85.

Terminating in the meandering carrier flow channel 83 is an injection terminal 86, via which particles can be injected into the carrier flow. Due to the narrowing and widening in the carrier flow channel 83 the sedimentizing of particles in the carrier flow channel 83 is countered, so that the suspended particles move uniformly and continuously.

The invention is not limited to the above described preferred embodiments. Rather a plurality of variants and modifications is possible, which can likewise make use of the inventive idea and therefore fall within the range of protection.

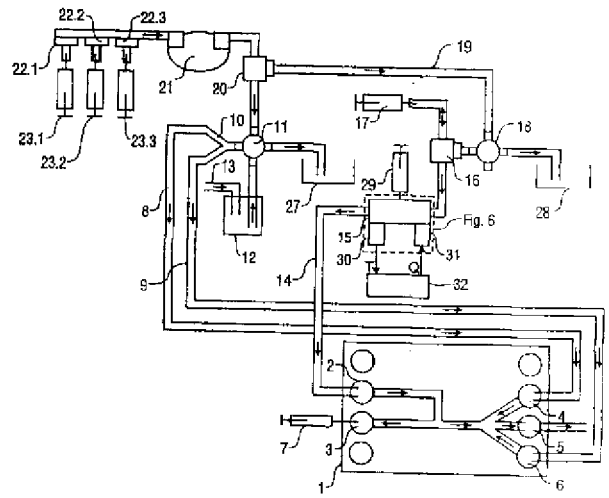

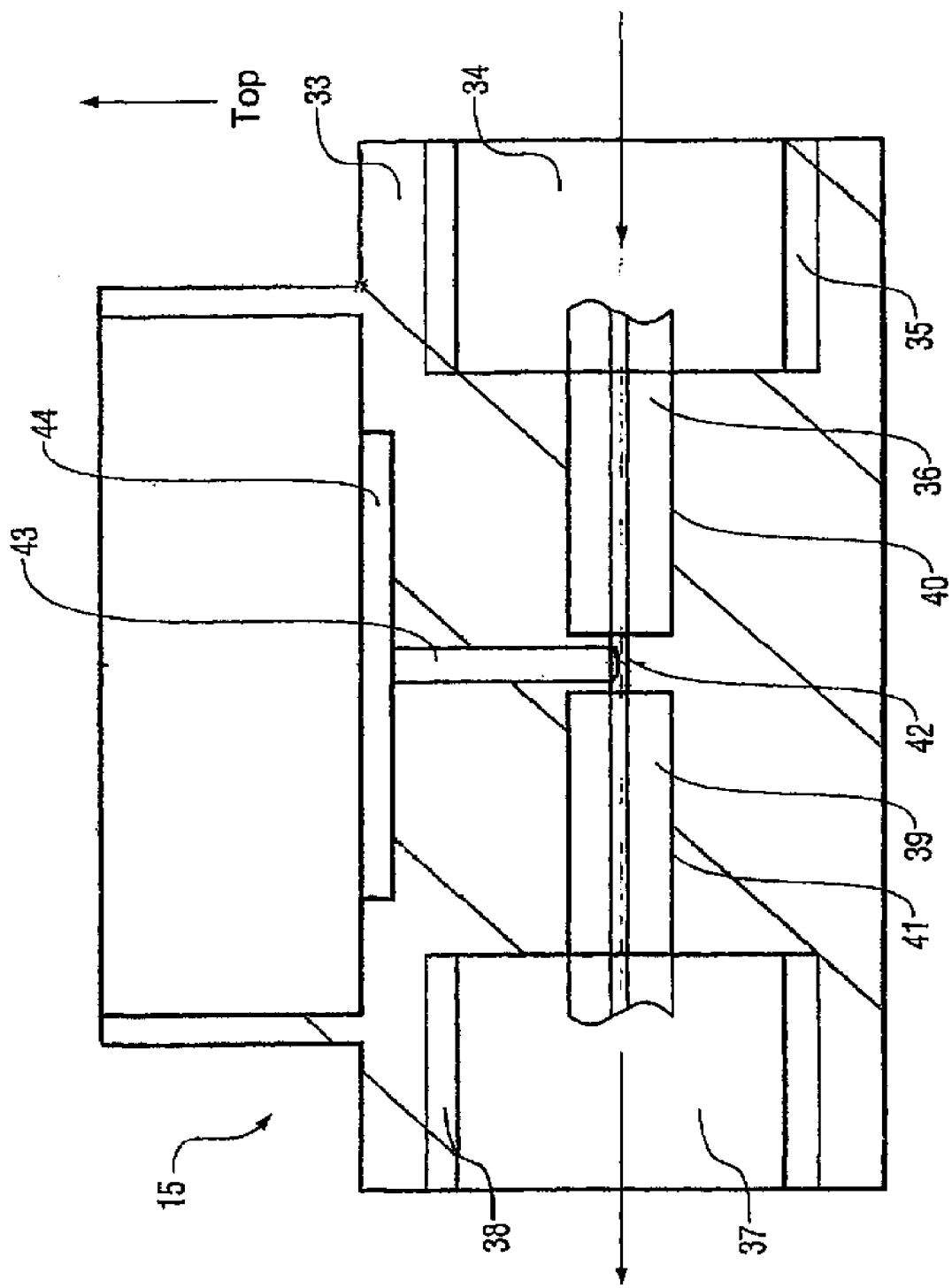

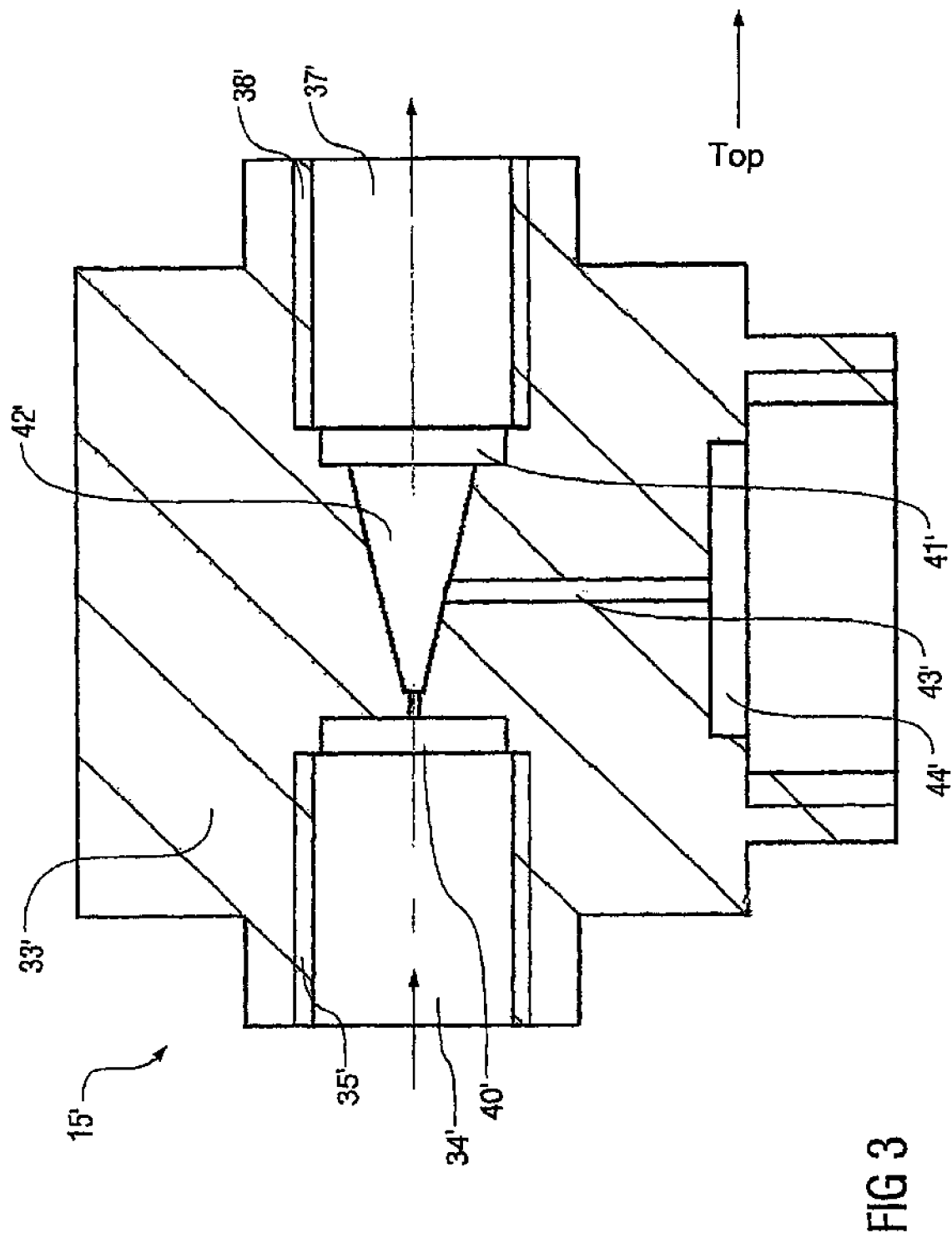

The invention claimed is:

1. A particle injector for introducing particles into a carrier flow of a microfluidic system, comprising: at least one inlet for receiving the carrier flow, at least one outlet for discharging the carrier flow with the introduced particles, at least one carrier flow channel, connecting the inlet to the outlet, wherein the carrier flow channel has substantially no dead volume and at least one injection channel terminating in the carrier flow channel for introducing the particles into the carrier flow, wherein the injection channel has a feeding-in aid for an injection needle.

2. The particle injector as claimed in claim 1, wherein the injection channel terminates obtusely in the carrier flow channel.

3. The particle injector as claimed in claim 1, wherein the injection channel terminates substantially right-angled in the carrier flow channel.

4. The particle injector as claimed in claim 1 wherein the inlet and the outlet have a substantially same-size cross-section.

5. The particle injector as claimed in claim 1, wherein the inlet has a centering aid to arrange a line coaxially to the carrier flow channel on the inlet.

6. The particle injector as claimed in claim 5, wherein the centering aid comprises a substantially hollow-cylindrical take-up, which borders the carrier flow channel and is arranged coaxially to the carrier flow channel, whereby the inner diameter of the take-up is larger by the wall thickness of the line than the inner diameter of the carrier flow channel.

7. The particle injector as claimed in claim 1, wherein the particle injector has a top side and a bottom side and said injection channel is arranged on said top side.

8. The particle injector as claimed in claim 1, wherein the injection channel has a cross-section, which widens away from the inlet towards the outlet.

9. The particle injector as claimed in claim 1, wherein the inlet of the carrier flow channel is located below the outlet of the carrier flow channel such that carrier flow through the particle injector is in a substantially upward direction.

10. The particle injector as claimed in claim 1, wherein the injection channel has a cross-section narrowing to the carrier flow channel.

11. The particle injector as claimed in claim 1, wherein the feeding-in aid has funnel-shaped cross-section widening of the injection channel.

12. The particle injector as claimed in claim 1, wherein the feeding-in aid comprises a detachably attached separate component, in which a funnel-shaped feed opening is arranged, said opening terminating in the injection channel in a mounted state.

13. The particle injector as claimed in claim 1, wherein the carrier flow channel has a substantially shoulder-free inner contour.

14. The particle injector as claimed in claim 1, wherein the carrier flow channel has a volume of between 0.02 .mu.l and 1 ml.

15. The particle injector as claimed in claim 1, wherein the particle injector is adapted to be autoclaved.

16. The particle injector as claimed in claim 1, wherein the particle injector at least partially comprises a material selected from the group consisting of polyether ether ketone, polycarbonate, ceramic and metal.

17. The particle injector as claimed in claim 1, wherein the particle injector at least partially comprises a heat-conductive material.

18. The particle injector as claimed in claim 17, wherein the particle injector is connected with at least one of a temperature sensor and a tempering element.

19. The particle injector as claimed in claim 1, wherein at least one the inlet and the outlet has a thread for attaching a line.

20. The particle injector as claimed in claim 1, wherein the outlet has a centering aid to arrange a line coaxially to the carrier flow channel on the outlet.

21. The particle injector as claimed in claim 1, wherein the particle injector is adapted to inject biological cells into the carrier flow of a cell sorter.

* * * * *

UNITED STATES PATENT AND TRADEMARK OFFICE
CERTIFICATE OF CORRECTION

PATENT NO. : 7,510,685 B2
APPLICATION NO. : 10/556017
DATED : March 31, 2009
INVENTOR(S) : Torsten Muller, Stefan Hummel and Annete Pfennig It is certified that error appears in the above-identified patent and that said Letters Patent is hereby corrected as shown below:

The title page should be deleted and substitute therefor the attached title page.

Delete Figures 1, 2, 3, 5 and 6 and replace with the Figures 1, 2, 3, 5 and 6 as shown on the attached pages.

Signed and Sealed this

Second Day of June, 2009

JOHN DOLL
*Acting Director of the United States Patent and Trademark Office*

(12) United States Patent
Müller et al.

(10) Patent No.: US 7,510,685 B2
(45) Date of Patent: Mar. 31, 2009

(54) PARTICLE INJECTOR FOR A CELL SORTER

(75) Inventors: Torsten Müller, Berlin (DE); Stefan Hummel, Haseldorf (DE); Annette Pfennig, Berlin (DE)

(73) Assignee: Evotec Technologies GmbH (DE)

( * ) Notice: Subject to any disclaimer, the term of this patent is extended or adjusted under 35 U.S.C. 154(b) by 386 days.

(21) Appl. No.: 10/556,017

(22) PCT Filed: May 10, 2004

(86) PCT No.: PCT/EP2004/004984

§ 371 (c)(1),
(2), (4) Date: Jan. 23, 2006

(87) PCT Pub. No.: WO2004/099760

PCT Pub. Date: Nov. 18, 2004

(65) Prior Publication Data

US 2006/0115890 A1    Jun. 1, 2006

(30) Foreign Application Priority Data

May 9, 2003 (DE) .................... 103 20 870

(51) Int. Cl.
*B01L 3/00* (2006.01)
(52) U.S. Cl. .................................................. 422/99
(58) Field of Classification Search ............. 422/99
See application file for complete search history.

(56) References Cited

U.S. PATENT DOCUMENTS

| | | | |
|---|---|---|---|
| 4,954,715 A | 9/1990 | Zöld | |
| 5,138,181 A | 8/1992 | Lefevre et al | |
| 5,351,118 A | 9/1994 | Spinell | |
| 5,489,506 A | 2/1996 | Crane | |
| 5,542,305 A | 8/1996 | Hollinger | |

(Continued)

FOREIGN PATENT DOCUMENTS

| | | |
|---|---|---|
| DE | 100 05 735 A1 | 8/2001 |
| WO | WO 02/11888 A2 | 2/2002 |
| WO | WO 02/065121 A1 | 8/2002 |
| WO | WO 02/081934 A2 | 10/2002 |
| WO | WO 03/078065 A1 | 9/2003 |

OTHER PUBLICATIONS

Müller, et al., "A 3-D microelectrode system for handling and caging single cells and particles", Biosensors & Bioelectronics 14 (1999), pp. 247-256.

*Primary Examiner*—Walter D Griffin
*Assistant Examiner*—Bobby Ramdhanie
(74) *Attorney, Agent, or Firm*—Caesar, Rivise, Bernstein, Cohen & Pokotilow, Ltd.

(57) ABSTRACT

The invention relates to a particle injector for introducing particles into a carrier flow of a microfluidic system, especially for injecting biological cells into the carrier flow of a cell sorter. The particle injector includes an inlet for receiving the carrier flow, an outlet for discharging the carrier flow including the introduced particles, a carrier flow channel which connects the inlet to the outlet, and an injection channel flowing into the carrier flow channel for introducing the particles into the carrier flow. The inventive particle injector is characterized in that the carrier flow channel has substantially no dead volume.

21 Claims, 12 Drawing Sheets